(12) United States Patent
Sakthivel et al.

(10) Patent No.: US 7,381,651 B2
(45) Date of Patent: Jun. 3, 2008

(54) PROCESSES FOR MONITORING THE LEVELS OF OXYGEN AND/OR NITROGEN SPECIES IN A SUBSTANTIALLY OXYGEN AND NITROGEN-FREE PLASMA ASHING PROCESS

(75) Inventors: Palanikumaran Sakthivel, Odenton, MD (US); Thomas J. Buckley, Frederick, MD (US); Alan F. Becknell, Ellicott City, MD (US)

(73) Assignee: Axcelis Technologies, Inc., Beverly, MA (US)

( * ) Notice: Subject to any disclaimer, the term of this patent is extended or adjusted under 35 U.S.C. 154(b) by 0 days.

(21) Appl. No.: 11/386,327

(22) Filed: Mar. 22, 2006

(65) Prior Publication Data

US 2007/0221620 A1  Sep. 27, 2007

(51) Int. Cl.
*H01L 21/461* (2006.01)
*H01L 21/302* (2006.01)

(52) U.S. Cl. .................... 438/706; 438/710; 438/714; 438/725

(58) Field of Classification Search ............... None
See application file for complete search history.

(56) References Cited

U.S. PATENT DOCUMENTS

| 4,776,690 | A | * | 10/1988 | Quimby ............... 356/72 |
|---|---|---|---|---|
| 5,708,957 | A | * | 1/1998 | Chuang et al. ........ 422/82.07 |
| 6,638,875 | B2 | | 10/2003 | Han et al. ............. 438/725 |
| 6,864,109 | B2 | * | 3/2005 | Chang et al. ........... 438/16 |
| 6,951,823 | B2 | | 10/2005 | Waldfried et al. ...... 438/710 |
| 2002/0140932 | A1 | * | 10/2002 | Satou et al. ........... 356/311 |
| 2004/0235299 | A1 | * | 11/2004 | Srivastava et al. ..... 438/689 |
| 2004/0238123 | A1 | * | 12/2004 | Becknell et al. ....... 156/345.33 |
| 2005/0019964 | A1 | * | 1/2005 | Chang et al. ........... 438/16 |

* cited by examiner

*Primary Examiner*—Duy-Vu N Deo
(74) *Attorney, Agent, or Firm*—Cantor Colburn LLP

(57) ABSTRACT

Processes for monitoring the levels of oxygen and/or nitrogen in a substantially oxygen and nitrogen-free plasma ashing process generally includes monitoring the plasma using optical emission. An effect produced by the low levels of oxygen and/or nitrogen species present on other species generally abundant in the plasma is monitored and correlated to amounts of oxygen and nitrogen present in the plasma. This so-called "effect detection" process monitors perturbations in the spectra specifically associated with species other than nitrogen and/or oxygen due to the presence of trace amounts of oxygen and/or nitrogen species and is used to quantitatively determine the amount of oxygen and/or nitrogen at a sensitivity on the order of 1 part per million and potentially 1 part per billion.

19 Claims, 7 Drawing Sheets

PROCESSES FOR MONITORING THE LEVELS OF OXYGEN AND/OR NITROGEN SPECIES IN A SUBSTANTIALLY OXYGEN AND NITROGEN-FREE PLASMA ASHING PROCESS

BACKGROUND

The present disclosure generally relates to plasma ashing processes for selectively removing photoresist, organic overlayers, and polymer residues from a substrate surface, and in particular, processes for monitoring oxygen and/or nitrogen species in a substantially oxygen and nitrogen free plasma.

Ashing is a plasma mediated stripping process by which photoresist, organic overlayers, and/or polymer residues are stripped or removed from a substrate upon exposure to the plasma. Ashing generally occurs after an etching process has been performed in which the photoresist material is used as a photomask for etching a pattern into the substrate. The ashing process is also used to remove other organic layers such as the anti-reflection coating (ARC), if present. Additionally, the ashing process may be performed for removal of misaligned resist patterns ("rework wafers") and in lift-off processes. It is well known that the process steps occurring prior to ashing may modify the surface of the photoresist and ARC, and/or form polymers/residues. It is highly desirable when ashing that complete removal of the photoresist and other organic overlayers, polymers/residues occur as quickly as possible without loss of any of the materials comprising the underlayers and/or the materials that form the substrate.

It is important to note that ashing processes significantly differ from etching processes. Although both processes may be plasma mediated, an etching process is markedly different in that the plasma chemistry is deliberately chosen to permanently transfer an image into the substrate by removing portions of the substrate surface through openings in a photoresist mask. This type of plasma generally includes high-energy ion bombardment at low temperatures to remove selected portions of the substrate. Moreover, the portions of the substrate exposed to the high-energy ions are generally removed at a rate equal to or greater than the removal rate of the photoresist mask.

In contrast, ashing processes generally refer to selectively removing the photoresist mask and any polymers or residues formed during etching without removing portions of the underlying substrate. The ashing plasma chemistry is much less aggressive than etching chemistries and generally is chosen to remove the photoresist mask layer at a rate much greater than the removal rate of the underlying substrate. Moreover, most ashing processes heat the substrate to temperatures greater than 200° C. to increase the plasma reactivity. Thus, etching and ashing processes are directed to removal of significantly different materials and as such, require completely different plasma chemistries and processes. Successful ashing processes are not used to permanently transfer an image into the substrate. Rather, successful ashing processes are defined by the photoresist, polymer and residue removal rates without affecting and/or removing layers comprising the underlying substrate.

Ashing selectivity is defined as the relative removal rate of the photoresist and other organic overlayers, compared to the underlying layer. It is generally preferred to have an ashing selectivity of at least 20:1, wherein at least 20 times as much photoresist is removed as the underlying substrate. More preferably, the ashing selectivity is much greater than 100:1.

During plasma ashing processes, it is important to maintain a critical dimension (CD) for the various features within a tightly controlled specification as well as promote proper underlayer surface conditions for successful metal filling in the process steps occurring after photoresist and/or polymer/residue removal. Small deviations in the patterned profiles formed in the underlayers can adversely impact device performance, yield and reliability of the final integrated circuit. Traditionally, the ashing plasma has been generated from substantially oxygen and/or nitrogen containing gases. However, it has been found that these oxygen and/or nitrogen containing plasmas readily damage certain materials used in advanced integrated circuit manufacture. For example, oxygen-containing plasmas are known to raise the dielectric constant of low k dielectric underlayers during plasma processing. The increases in dielectric constant affects, among others, interconnect capacitance, which directly impacts device performance. Moreover, the use of oxygen-containing plasmas is generally less preferred for advanced device fabrication employing copper metal layers since the copper can be oxidized.

In order to overcome these problems, substantially oxygen-free and substantially nitrogen-free ashing plasma chemistries have been developed. By substantially oxygen-free it is generally meant that the plasma chemistry has less than about 50 parts per million (ppm) oxygen in the gas mixture defining the plasma, and by substantially nitrogen-free, it is generally meant that the plasma chemistry has less than about 10 ppm nitrogen in the gas mixture defining the plasma. Though oxygen-free plasma can be used to remove photoresist, it is desirable to use a substantially oxygen-free plasma to more effectively remove photoresist, organic overlayers, and polymers/residues from substrates containing low k dielectric materials without physically damaging the low k dielectric layer. Substantially oxygen-free and substantially nitrogen-free plasmas can be generated from hydrogen and helium gas mixtures, but tend to contain residual nitrogen due to the purity levels of gases generally used, and due to the relaxed standards for leak integrity of vacuum systems typically needed in plasma ashers. It is generally less preferred to have nitrogen present in any substantial quantity, since in some cases, it has been found that the use of plasmas containing nitrogen may alter and/or affect the chemical, mechanical, and electrical properties of the underlying substrate. For example, exposing carbon and/or hydrogen containing low k dielectric materials to plasmas generated from hydrogen, helium gas mixtures (containing substantial amounts of oxygen and/or nitrogen) can result in significant damage to the underlying substrate. Occasionally, the damage is not detected during a visual inspection such as a metrology inspection of the substrate after plasma processing. However, the damage can be readily demonstrated by a subsequent wet cleaning process, as may be typically employed in the integrated circuit manufacturing process undesirably after plasma ashing, wherein portions of the carbon and/or hydrogen-containing low k dielectric material are removed. The removed portions of the dielectric material are a source of variation in the critical dimension (CD) of the substrate feature and are frequently unacceptable, which then impacts overall device performance/yield. Moreover, even if a wet clean process is not included, the electrical and mechanical properties of the dielectric material may be changed by exposure to plasmas that contain substantial amounts of oxygen and/or nitrogen, thereby affecting operating performance. It is believed that carbon is depleted from the dielectric material during the plasma exposure, and the oxygen and/or nitrogen species contained therein damages the dielectric in such a way that it causes problems during subsequent metal filling processes, such as the creation of voids at the bottom of trench structures.

Because of the problems discovered due to the unintended presence of nitrogen found in the gas mixture used for forming the substantially oxygen-free and substantially nitrogen-free plasmas as noted above as well as the sensitivity of the low k materials to the presence of nitrogen radicals and/or oxygen radicals, it is important to accurately monitor these species during plasma processing.

Optical emission spectroscopy is a well-known procedure for trace element detection. However, it is difficult to accurately detect the levels of nitrogen and/or oxygen species in the plasma using the relatively unsophisticated spectrometers that are currently employed in the industry to cost-effectively monitor the specific wavelengths associated with the major emission signal for these species, e.g., $N_2$ at 335-337 nanometers (nm) and O at 777 nm. The low cost, unsophisticated optical emission spectrometers currently used by those in the art are generally unacceptable for detecting the relatively low levels of nitrogen and oxygen because of poor resolution and lack of sensitivity inherent to these small footprint type spectrometers. For example, it is very difficult to differentiate and quantify the concentration of oxygen species at concentrations less than 50 parts per million (ppm) using these spectrometers. More sophisticated spectrometers are generally impractical due to the added costs to the plasma ash equipment, the larger foot-print, the complexity of operation as well as the maintenance, calibration, and integration issues associated with these types of equipment.

FIG. 1 illustrates the optical emission spectra in the range of 750 nm to 800 nm for a hydrogen-helium (He—$H_2$) plasma in the presence of varying levels of oxygen. The 0.01 ppm level of oxygen was estimated based on a curve fit whereas the 10-100 ppm levels of oxygen were prepared by gas mixing with 'low flow' mass flow controllers. As can be seen from the graph, the oxygen emission signal at 777 nm can be readily distinguished at amounts greater than 20 ppm. However, at less than 20 ppm, resolution and discrimination between the varying amounts is poor.

FIG. 2 graphically illustrates another example wherein the optical emission spectra in the range of 300 nm to 350 nm for a hydrogen-helium (He—$H_2$) plasma was monitored in the presence of varying levels of nitrogen. As can be seen from the graph, at nitrogen levels less than 10-20 ppm, the resolution and discrimination between the varying amounts is poor and not reliable.

Accordingly, there is a need to have an accurate process for monitoring the amounts of nitrogen and/or oxygen in a substantially oxygen and/or nitrogen free plasma by a commercially viable method such as using commercially available low-cost, unsophisticated optical emission spectrometers so that the plasma ashing process can be monitored to prevent damage to the underlying low k structure while providing a robust process for removing the photoresist and any polymers or residues. Desirably, the process should be capable of accurately detecting oxygen levels less than 50 ppm, and nitrogen levels less than 10 ppm.

BRIEF SUMMARY

Disclosed herein are processes for monitoring oxygen and/or nitrogen species in a substantially oxygen and nitrogen-free plasma ashing process of a substrate. In one embodiment, the process comprises forming reactive species by exposing a plasma gas composition to an energy source to form a plasma substantially free from nitrogen species and oxygen species; monitoring optical emission signals specifically associated with one or more major components of the plasma gas composition; and correlating perturbations in the monitored optical emission signals affected by the presence of oxygen and/or nitrogen species in the plasma gas composition to a specific amount of the oxygen and/or nitrogen species in the plasma.

In another embodiment, a process for monitoring oxygen and/or nitrogen species in a substantially oxygen and nitrogen-free plasma ashing process of a substrate comprises monitoring a ratio of optical emission signals specifically associated with a ratio of major components of the plasma gas composition in the presence of a fixed amount of oxygen and in the absence of the fixed amount of oxygen; and calculating a ratio of the ratios during the substantially oxygen and nitrogen-free plasma ashing process and correlating an amount of oxygen and nitrogen species in the plasma from the model curve using the ratio of the ratios.

In yet another embodiment, a process for monitoring nitrogen and/or oxygen species at levels less than 100 ppm in substantially oxygen and/or nitrogen free plasmas comprises measuring spectral perturbations produced by the oxygen and/or nitrogen species present at levels less than 100 ppm in the substantially oxygen and/or nitrogen free plasma on other species that define major components of the plasma; and correlating the spectral perturbation affected by the presence of the oxygen and/or nitrogen species in the plasma gas composition to a specific amount of oxygen and nitrogen in the plasma.

In still another embodiment, a process for detecting contamination levels of nitrogen and oxygen in a gas mixture comprising helium and hydrogen comprise generating a plasma with the gas mixture; monitoring optical emission signals specifically associated with hydrogen and helium species in the plasma; and correlating perturbations in the monitored optical emission signals affected by the presence of oxygen and/or nitrogen species in the plasma gas composition to a specific amount of the oxygen and/or nitrogen species in the plasma.

These and other objects, advantages and features of the disclosure will become better understood from the detailed description of the disclosure that is described in conjunction with the accompanying drawings.

DETAILED DESCRIPTION

Processes for monitoring nitrogen and/or oxygen species at levels less than 100 ppm in substantially oxygen and/or nitrogen free plasmas generally include monitoring an effect produced by low levels of oxygen and/or nitrogen species present in the plasma on other species generally abundant in the plasma. This so-called "effect detection" process monitors perturbations in the spectra specifically associated with species other than nitrogen and/or oxygen due to the presence of trace amounts of the oxygen and/or nitrogen species.

A typical substantially oxygen and nitrogen-free plasma ashing process includes generating reactive species substantially free of oxygen and/or nitrogen species from a plasma gas mixture and exposing a substrate to the reactive species. Exemplary substantially oxygen and nitrogen-free plasma ashing processes are described in U.S. Pat. No. 6,951,823, incorporated by reference herein in its entirety. Exemplary apparatuses for generating substantially oxygen and nitrogen-free plasma ashing processes are described in co-pending U.S. patent application Ser. No. 10/249,962, incorporated herein by reference in its entirety. The substantially oxygen and nitrogen-free plasma ashing processes are advantageous in that the ash rate of photoresist and/or other organic overlayers is enhanced, improved stability is provided, and selectivity is improved while effectively preventing and/or minimizing damage to underlying copper metal layers and/or low k dielectric layers. The substantially oxygen and nitrogen-free plasma ashing processing of substrates provides a more economical solution than plasma ashing processes that are completely free of any oxygen and nitrogen species. For example, a lower leak rate specification can be tolerated for the plasma chamber and the gases used can have a lower purity specification with regard to oxygen and nitrogen impurities, thereby providing the end user with a means for lowering costs.

In the substantially oxygen and nitrogen-free plasma ashing processes, it is generally preferred to maintain the oxygen levels at less than 15 ppm, and more specifically, between about 5 ppm and 15 ppm, for typical ash temperatures, e.g., ashing temperatures greater than about 200° C. The nitrogen levels are maintained at less than 1 ppm for the typical ash temperatures. As would be appreciated by those in the art, lower ashing temperatures (e.g., less than about 200° C.) tolerate (are less damaging) greater levels of oxygen and nitrogen. For reasons discussed in the background section, previous methods of monitoring the primary emission signals specifically associated with oxygen (e.g., 777 nm) and/or nitrogen (e.g. 335 nm) are inadequate for monitoring oxygen levels less than 20 ppm and/or nitrogen levels less than 10 ppm.

Figure 1:
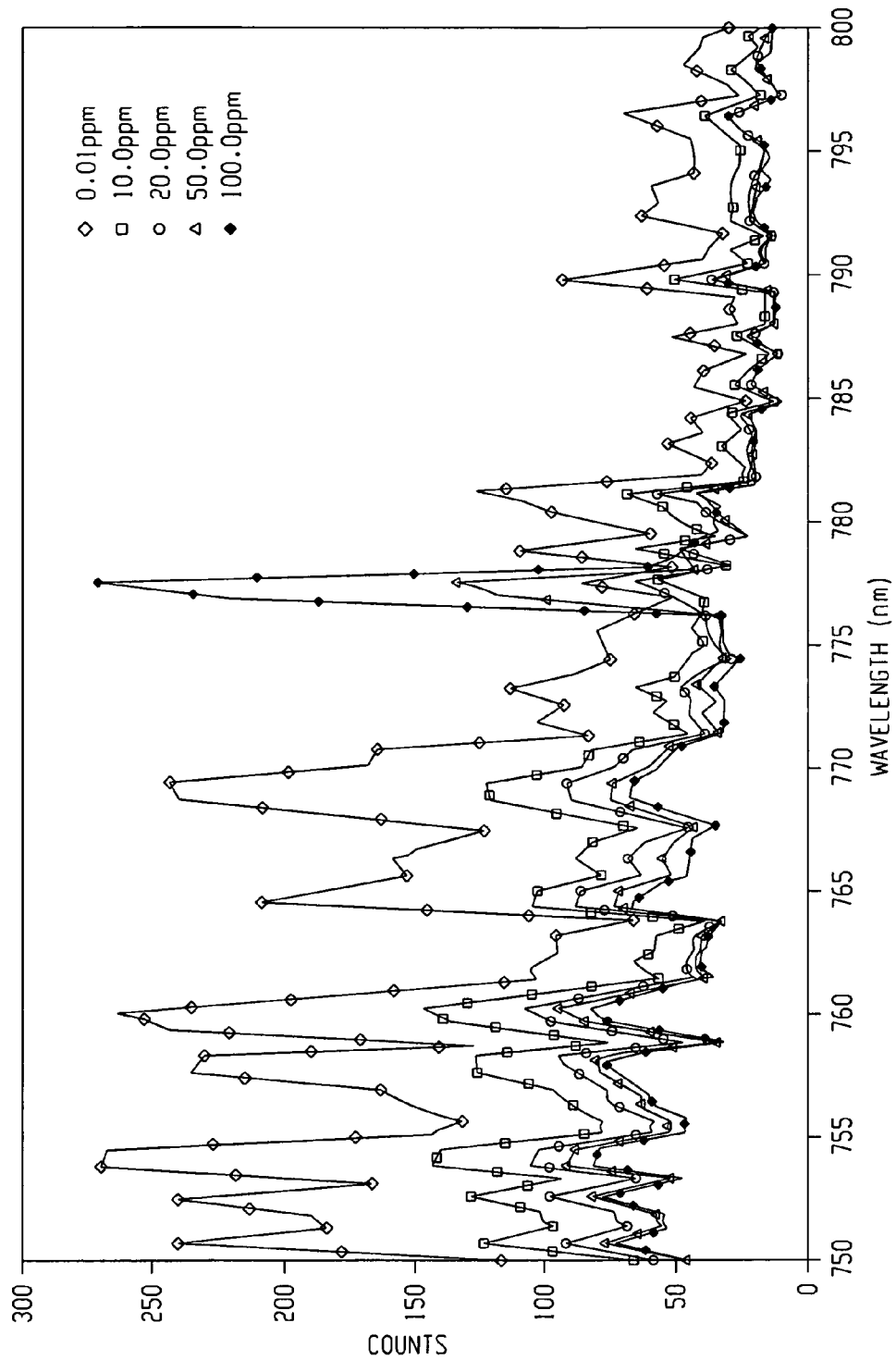
FIG. 1 graphically illustrates an emission spectrum from 750 nm to 800 nm of a hydrogen-helium plasma at varying levels of oxygen, which includes an emission signal specifically associated with oxygen at about 777 nm.
Figure 2:
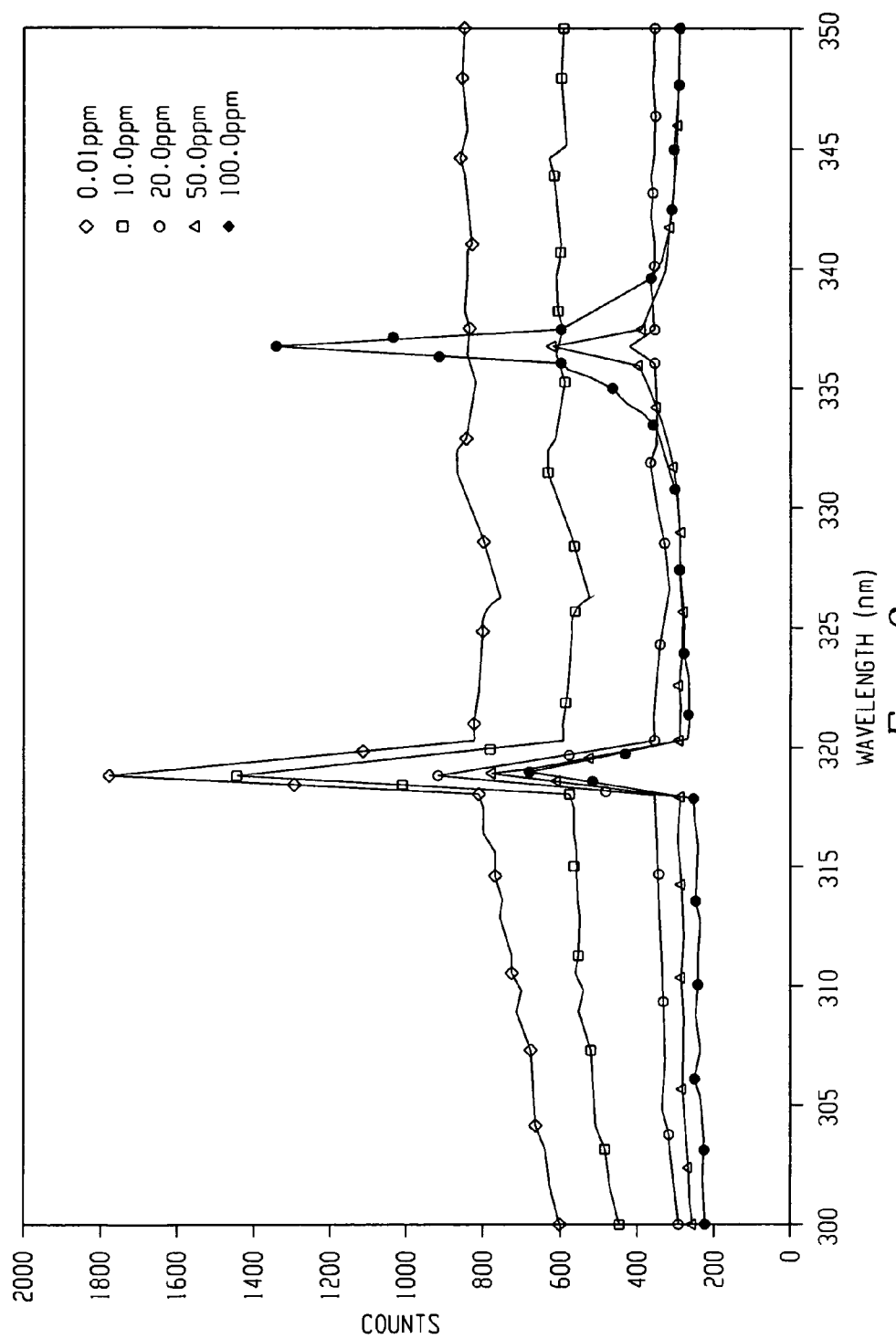
FIG. 2 graphically illustrates an emission spectrum from 300 nm to 350 nm of a hydrogen-helium plasma at varying levels of nitrogen which includes an emission signal specifically associated with nitrogen at about 335-337 nm.
Figure 3:
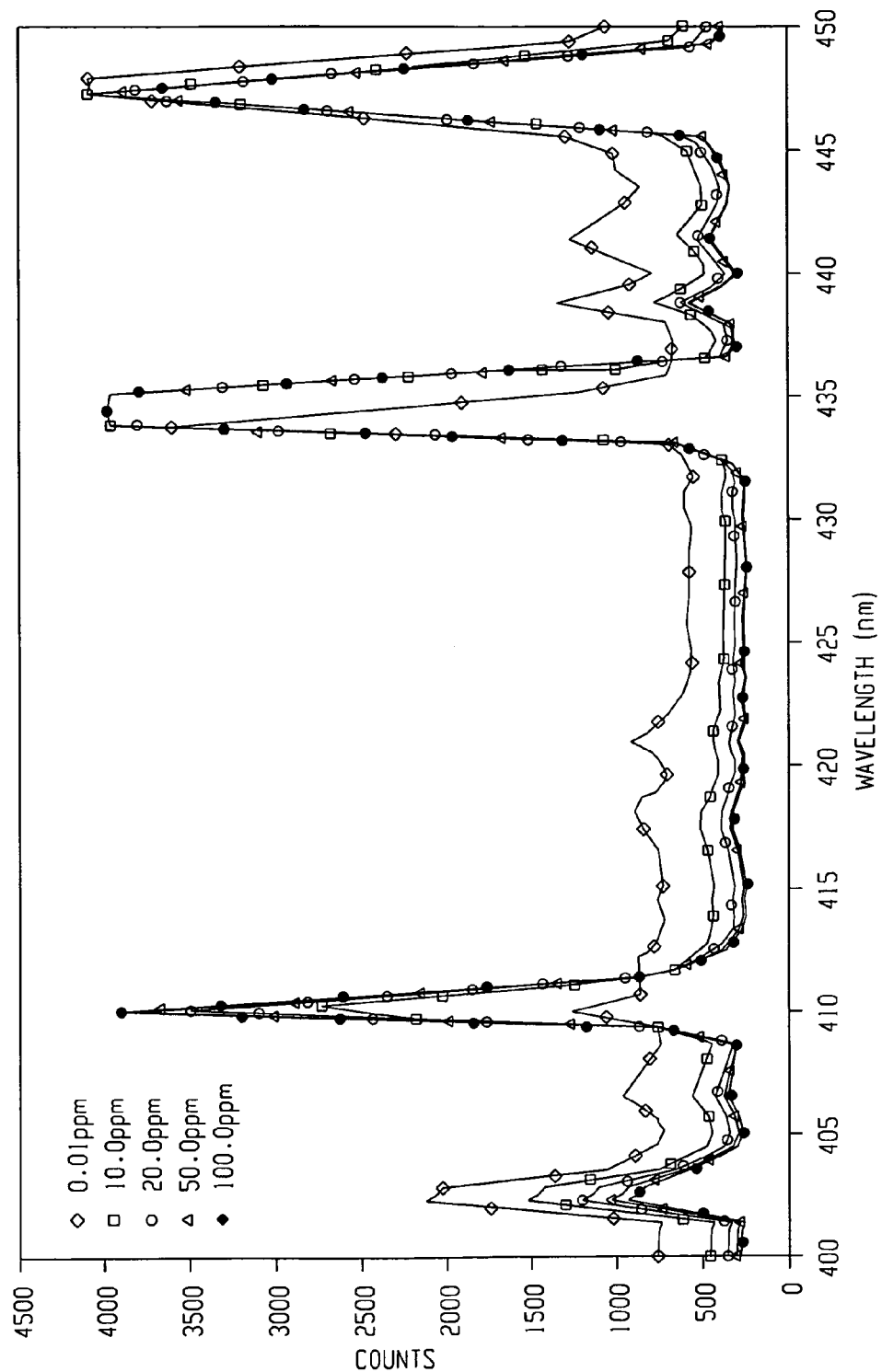
FIG. 3 graphically illustrates an emission spectrum from 400 nm to 450 nm of a hydrogen-helium plasma at varying levels of hydrogen, which includes an emission signal specifically associated with hydrogen at about 410 nm.

Referring now to FIG. 3, a graph is provided that illustrates the optical emission spectra in the range of 400 nm to 450 nm for a hydrogen-helium (He—$H_2$) plasma in the presence of varying levels of oxygen (as opposed to the optical emission spectra of 750 nm to 800 nm as in FIG. 1). One of the primary emission signals specifically associated with hydrogen occurs at about 410 nm whereas one of the primary emission signals of helium occurs at about 403 nm. In contrast to the process described in relation to FIG. 1, which monitored the emission signals specifically associated with oxygen, we have found that low levels of oxygen and/or nitrogen significantly affect the primary emission signals specifically associated with a species generally abundant in the plasma (i.e., a major component) and can be used to provide an accurate means for monitoring oxygen and/or nitrogen in the plasma. Because of this, the changes in the spectrum can be correlated to specific amounts of oxygen and/or nitrogen in the plasma.

As demonstrated in FIG. 3, the distinction between an oxygen concentration of 10 and 20 ppm is readily resolved by simply monitoring the hydrogen emission signal at 410 nm, which was previously not possible by monitoring the primary emission signal specifically associated with the particular low level of oxygen, for example. As expected, the peak maximum/area of the hydrogen emission signal at 410 nm increases with increasing oxygen levels and is at a sensitivity on the order of parts per million. Likewise, the peak maximum/area specifically associated with helium at about 403 nm decreases with increasing oxygen levels and is also at a sensitivity on the order of parts per million. Thus, monitoring any one of the signals associated with a species abundant in the plasma can be used to better monitor the levels of oxygen in the plasma and at levels that could not be resolved in prior art optical emission spectroscopy processes.

It is also observed in FIG. 3 that the magnitude of the background subtracted hydrogen peak at 0.01 ppm (concentration based on a curve fit) is at about 510 counts. We have found that a much lower count level is sufficient to provide effective resolution. For example, a background subtracted signal of only 50 counts is generally sufficient to distinguish between line peaks, thereby suggesting that an extension in detection limits by at least an order of magnitude can be obtained, at least for oxygen. In other words, the practical limits of detection using this method for detecting oxygen species in a hydrogen/helium plasma are at about 1 part per billion of oxygen in the mixture. Thus, the monitoring process enables one of skill in the art to carefully regulate and control the amount of oxygen in the plasma. For example, controlled amounts (as an additive) can be added to a pure gas mixture (free of any oxygen) during plasma ashing. In this manner, the plasma ashing process can be optimized for photoresist and/or residue removal without deleteriously affecting exposed low k structures, i.e., without surpassing the damage threshold.

While not wanting to be bound by theory, it is believed that the introduction and/or presence of trace amounts of oxygen (on the order of parts per billion) and/or nitrogen (on the order of parts per million) can perturb the emission spectra of the original gas mixture significantly by changing the plasma temperature of the mixture, thereby altering the energy transfer modes, dissociating, ionizing or exciting other species in the mixture, hence altering the original thermal equilibrium of the plasma, and radically changing the plasma chemistry.

Further improvement in process sensitivity is noted upon monitoring a ratio of the primary emission signals associated with the abundant species, e.g., for a helium and hydrogen gas mixture, the peaks associated with hydrogen and helium. The ratio of these peaks enables unambiguous detection of the change in magnitude caused by the presence of oxygen and/or nitrogen in the plasma, irrespective of differences in the collection and transfer optics or window 'fogging' effects. Preferably, the emission peaks chosen for calculating the ratio are in close proximity. Using the gas mixture of hydrogen and helium as an example, the emission peaks associated with hydrogen (H) at 410 nm and helium (He), at 403 nm can be monitored; a difference of about 7 nm. Alternatively, the ratio can be determined by monitoring the hydrogen peak at 434 nm and the helium peak at 447 nm; a peak difference of about 13 nm. The emission signal of hydrogen ($H_2$) at 463 nm behaves in a similar manner to the helium peak, and consequently, can be used in the ratio with hydrogen (H). Because of this, the ratio of $H/H_2$ can be used to accurately detect the levels of oxygen. It should also be noted that this technique is very different from actinometry, which uses a wavelength corresponding to a deliberately introduced known trace amount of a non-reactive, non-perturbative gas to normalize the amount of species of interest. In our case, the species of interest is already a trace amount, and the amount of this species present in the mixture is not known a priori. A similar trend is seen with the addition of trace amounts of nitrogen, though the 'effect' response is less sensitive than that observed with oxygen.

As previously noted, the substantially oxygen and nitrogen-free plasma ashing process for effectively stripping photoresist and/or post etch residues without damaging low k materials utilizes about 5 to about 15 ppm of oxygen and less than 1 ppm of nitrogen, at standard plasma ash temperatures of greater than about 200° C. Inadvertent introduction of nitrogen/oxygen into the plasma mixture generally occurs through a compromise in the leak integrity, or due to a contaminated gas supply. To calibrate the 'effect' detection on the ratio of H/He, for example, known amounts of compressed dry air (CDA) can be added to the system with a low flow-low mass flow controller to simulate a leak or a contaminated gas supply.

Figure 4:
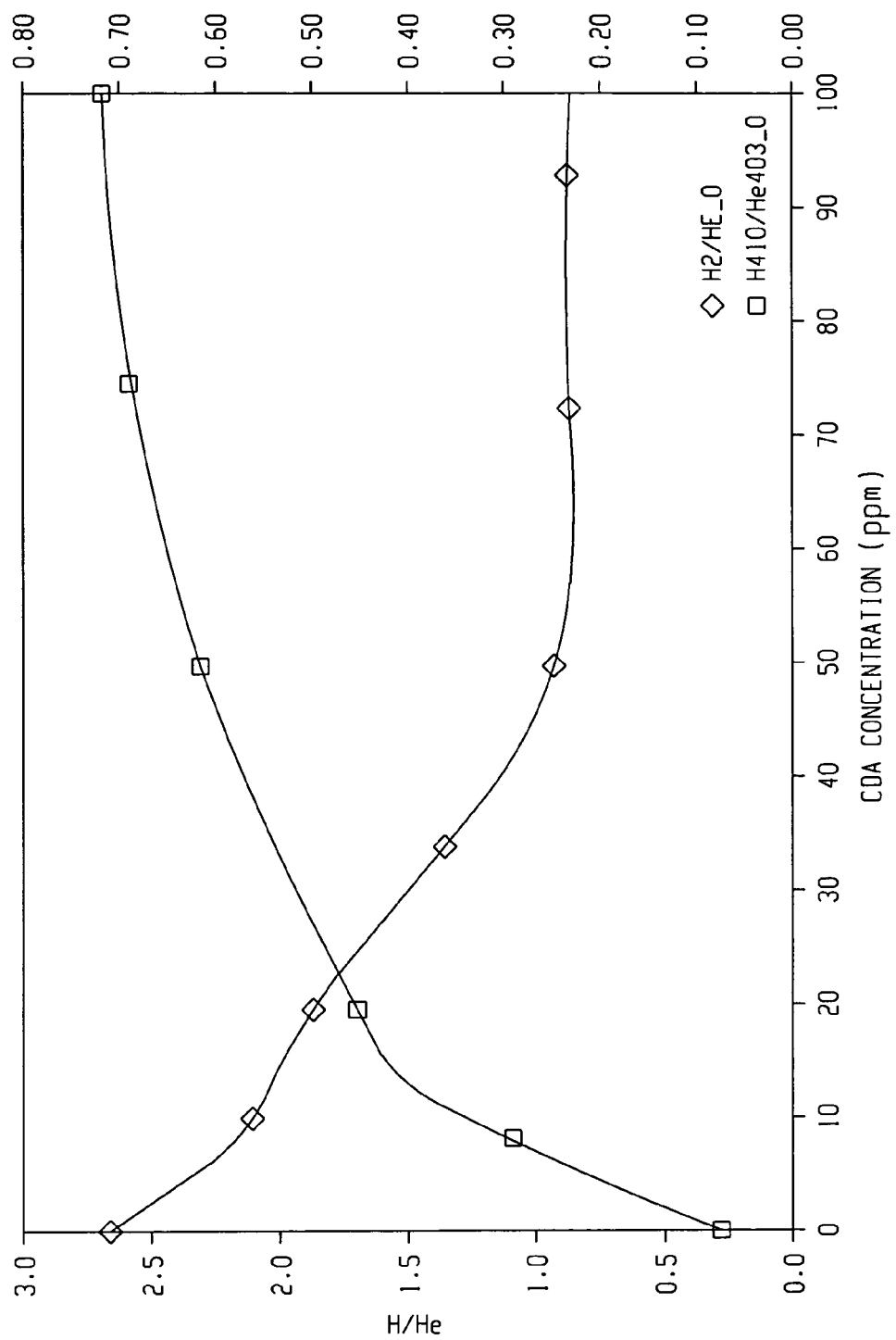
FIG. 4 graphically illustrates a measured concentration of compressed dry air (CDA) added to a hydrogen/helium plasma as a function of a ratio of the emission signal of hydrogen at 410 nm to helium at 403 nm; and a ratio of the emission signals of $H_2$ (463 nm) and He (403 nm)

FIG. 4 shows the rapid increase in H/He, the 'effect detection' parameter for increasing CDA concentration in the 0-20 ppm regime. The only source of oxygen in the H/He gas mixture was the CDA. Similarly, the effect on the $H_2$/He ratio is also plotted in the graph, showing an inverse relationship. While the ratio is a reasonable way to estimate the presence of nitrogen/oxygen in the system, it is difficult to do so with great precision due to the great sensitivity in the sub—10 ppm regime, and because of other factors such as differences in the spectral response of different spectrographs (particularly when using low cost versions), surface recombination effects on the plasma tube, and the imprecise nature of introducing such a small amount of CDA into the mixture during initial calibration and setup.

Figure 5:
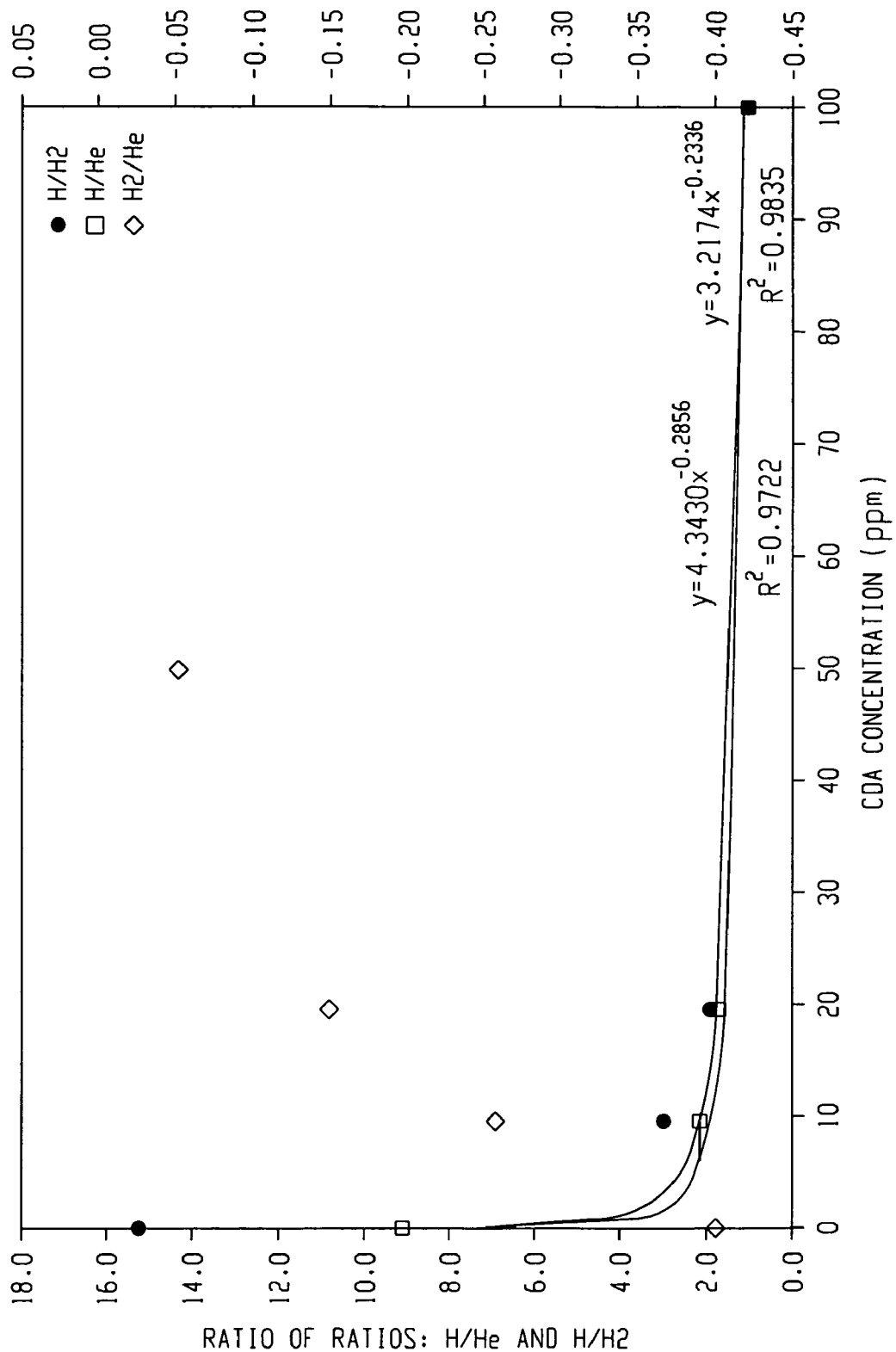
FIG. 5 graphically illustrates that a plot of the ratio of ratios as a function of CDA concentration enables prediction of the level of impurity (leak or CDA) through an equation resulting from the curve fit.

An improvement to estimate the presence of contaminants is to determine the change in the H/He ratio, for example, when a known amount of oxygen additive is added to the mixture and in the absence of the oxygen additive. This so-called 'ratio of ratios' can then be computed by obtaining the H/He in the presence and absence of a fixed amount of oxygen, e.g., a ratio of ratios at 10 ppm and 0 ppm of oxygen in the mixture. By finding the ratio of ratios at different concentrations of CDA, there is further amplification of the 'effect' at low concentrations, while it is rendered less sensitive to surface effects, differences in spectral response of detectors, and the like, and is dependent only on the level of residual impurities. FIG. 5 illustrates the 'ratio of ratio' technique, where a plot of the ratio of ratios as a function of CDA concentration enables prediction of the level of impurity/contaminant (leak or CDA) through an equation resulting from the curve fit. In this manner, a prediction can be made as to the level of oxygen and nitrogen impurity caused by a leak, for example.

Figure 6:
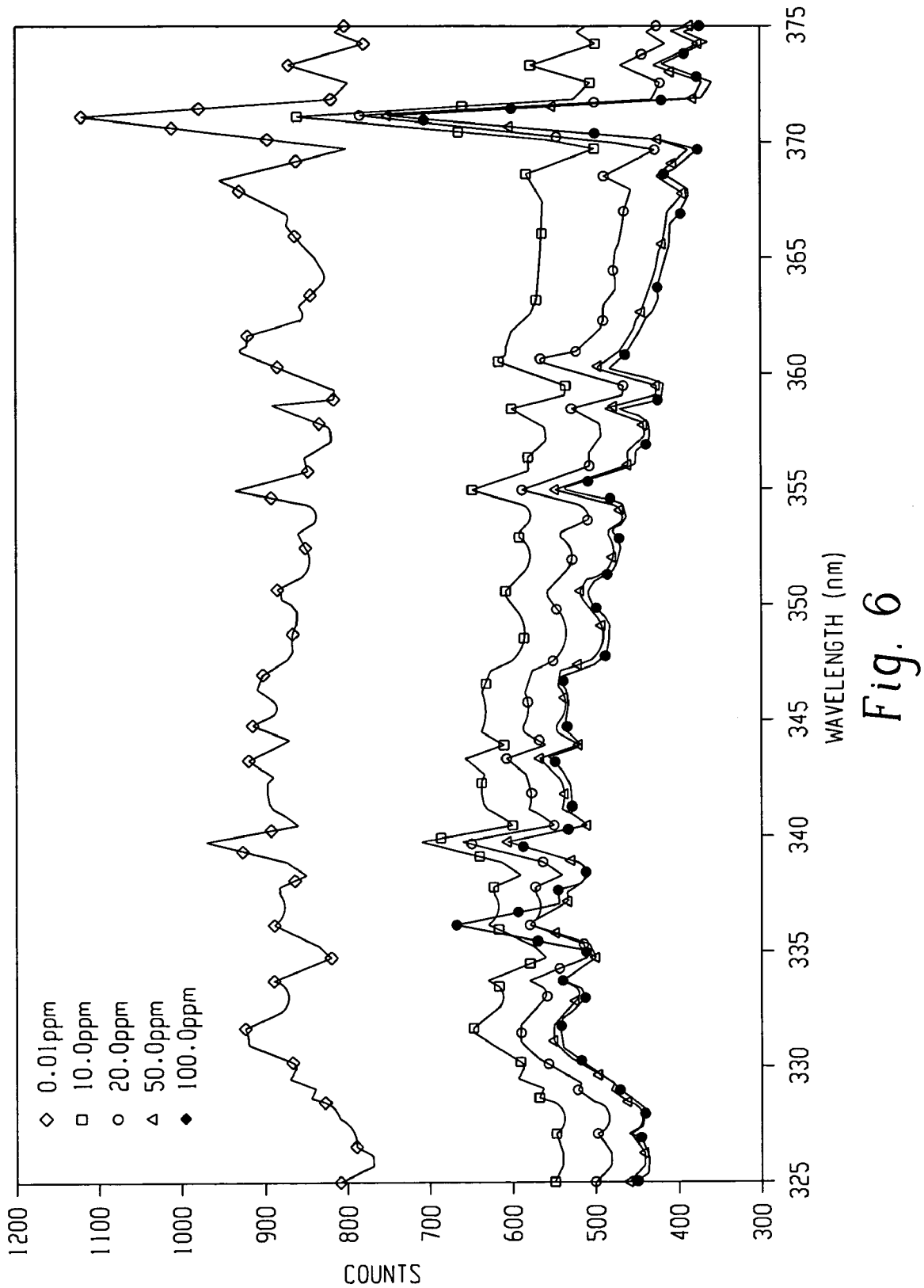
FIG. 6 graphically illustrates an emission spectrum from 325 nm to 375 nm of a hydrogen-helium plasma at varying levels of oxygen.

An alternate option for "effect detection" is to monitor the broadband continuum for high integration times of a charge coupled device (CCD) detector. As shown in FIG. 6, a relatively featureless portion (small peaks) of the broadband continuum of the same plasma is monitored. A significant shift in the baseline that is dependent on the concentration of oxygen is observed. Again, it is believed (while not being bound) the reason for this shift is a change in the free-electron collisions in the plasma influenced by shifts in plasma temperature and energy transfer channels. By averaging carefully selected featureless portions of the spectrum (and/or taking the ratio of different averages), it is possible to quantitatively detect the amounts of oxygen and/or nitrogen in the substantially oxygen and nitrogen-free plasma. This technique is also particularly suited to discriminate impurity levels at concentrations less than 50 ppm.

As noted above, the monitoring processes of the present disclosure are suitable for use in accurately monitoring the low levels of nitrogen and/or oxygen in substantially nitrogen and oxygen-free plasmas. The particular components of a substantially oxygen and nitrogen-free plasma gas mixture are generally selected by their ability to form a gas and plasma at plasma forming conditions. The gas mixture selected is substantially free from components that generate reactive oxygen species and reactive nitrogen species at plasma forming conditions. More preferably, the gas mixture is substantially free from oxygen-containing compounds and nitrogen-containing compounds. The gas mixture may include reactive gases such as a fluorine-bearing gas, a hydrogen-bearing gas, inert gases, and mixtures thereof. However, for certain low k materials, the presence of fluorine can be detrimental to the physical and chemical properties of the low k material. Suitable inert gases include argon, helium, neon and the like. Of these, helium is preferred. The substantially oxygen and nitrogen-free plasma generated from the gas mixture primarily reacts with carbon and other atoms in the photoresist, polymers/residues to form volatile compounds and/or rinse removable compounds.

Hydrogen-bearing gases suitable for use in the substantially oxygen and nitrogen-free plasma ashing process include those compounds that contain hydrogen. The hydrogen-bearing gases include hydrocarbons, hydrofluorocarbons, hydrogen gas or mixtures thereof. Preferred hydrogen-bearing gases exist in a gaseous state at plasma forming conditions and release hydrogen to form reactive hydrogen such as atomic hydrogen species under plasma forming conditions. The hydrocarbons or hydrofluorcarbons are generally unsubstituted or may be partially substituted with a halogen such as bromine, chlorine or fluorine. Examples of hydrogen-bearing hydrocarbon gases include methane, ethane and propane.

Preferred hydrogen-bearing gases are mixtures of a hydrogen gas and a noble gas. Examples of noble gases suitable for use in the process include helium. It is possible that other gases in Group VIII of the periodic table such as argon, neon, helium and the like may also serve the purpose. Although prior art oxygen-free plasmas generally used a forming gas composition that includes a hydrogen and nitrogen gas mixture, the use of substantial amounts of nitrogen gas in the process is expressly excluded. Consequently, since forming gas is hereinafter defined as a gas containing a mixture of hydrogen and nitrogen gases (nitrogen is generally greater than about 70% by volume or more in the forming gas mixture), the use of forming gas in the process is expressly excluded. Particularly preferable for use in the present disclosure is a gas mixture that includes hydrogen and helium gases. Helium atoms are light atoms and readily diffuse to the substrate, which results in excellent carrier characteristics for plasma generated reactive hydrogen species.

For safety reasons, the percentage of hydrogen gas in the gas mixture generally does not exceed about 5 percent by volume of the gas mixture. However, higher amounts of hydrogen are acceptable and sometimes preferred for increasing the photoresist and organic overlayer removal rate and selectivity. Preferably, the amount of hydrogen in the gas mixture is from about 1 to about 99 percent of the total volume. More preferably, the amount of hydrogen in the gas mixture is from about 3 to about 30 percent of the total volume.

Fluorine-bearing compounds in the plasma, if present, are less than about 10 percent of the total volume of the plasma gas mixture to maximize selectivity. It has been found that when the fluorine compounds are greater than about 10 percent by volume, polymerization of the photoresist byproducts can occur making the polymerized photoresist more difficult to remove. Preferred fluorine compounds include those compounds that generate fluorine reactive species when excited by the plasma. Preferably, the fluorine compound is a gas at plasma forming conditions and is selected from the group consisting of a compound having the general formula $C_xH_yF_z$, wherein x ranges from 1 to 4, y ranges from 0 to 9 and z ranges from 1 to 10, HF, $F_2$ and $SF_6$. Other fluorine bearing compounds that do not generate reactive nitrogen or oxygen species will be apparent to those skilled in the art. More preferably, the fluorine-bearing compound is $CF_4$, $C_2F_6$ or mixtures thereof.

As previously discussed, the substantially oxygen and nitrogen-free plasma is used to remove photoresist, post etch residues, and the like while not removing and/or deleteriously affecting the properties of the underlying materials. Photoresists are generally organic photosensitive films used for transfer of images to an underlying substrate. The present disclosure is generally applicable to monitoring plasma ashing processes applicable to removing those photoresists used in g-line, i-line, DUV, 193 nm, and 157 nm applications or the like. This includes, but is not limited to, novolaks, polyvinylphenols, acrylates, acetals, polyimides, ketals, cyclic olefins or the like. Other photoresist formulations suitable for monitoring in the present disclosure will be apparent to those skilled in the art in view of this disclosure. The photoresist may be positive acting or negative acting depending on the photoresist chemistries and developers chosen. Examples of organic overlayers include, but are not intended to be limited to, ARC, bottom anti-reflection coatings (BARC), and other proprietary sacrificial materials that are typically part of the mask ensemble.

The insulating layers used in advanced integrated circuits typically include the use of low k materials that have dielectric constants less than about 3.0. The low k dielectric materials can be spun onto the substrate as a solution or deposited by a chemical vapor deposition process. Important low k film properties include thickness and uniformity, dielectric constant, refractive index, adhesion, chemical resistance, thermal stability, pore size and distribution, coefficient of thermal expansion, glass transition temperature, film stress and copper diffusion coefficient. Low k dielectrics can be generally classified as dense and porous. Examples of porous low k dielectric materials include Nanoglass® (available from Honeywell Electronic Materials) and aerogels, porous MSQ, and other SiCOH-based porous materials. Examples of dense low k material include CORAL, AURORA, FlowFill and Black Diamond. Other suitable low k dielectric materials will be apparent to those skilled in the art in view of this disclosure. Advantageously, by carefully monitoring the plasma such that the concentration of oxygen is between about 5-15 ppm and nitrogen levels are below 1 ppm at typical ash temperatures, the beneficial properties of the above noted low k materials are maintained.

The process can be practiced in conventional plasma ashers. The disclosure is not intended to be limited to any particular plasma asher. For example, a plasma asher employing an inductively coupled plasma reactor could be used or a downstream plasma asher could be used. Preferably, the plasma asher is a downstream plasma asher, such as for example, microwave plasma ashers commercially available under the trade name RadiantStrip ES31k® from Axcelis Technologies, Inc. in Rockville, Md. More preferably, the plasma asher is adapted to selectively expose the substrate to reactive atomic species.

Figure 7:
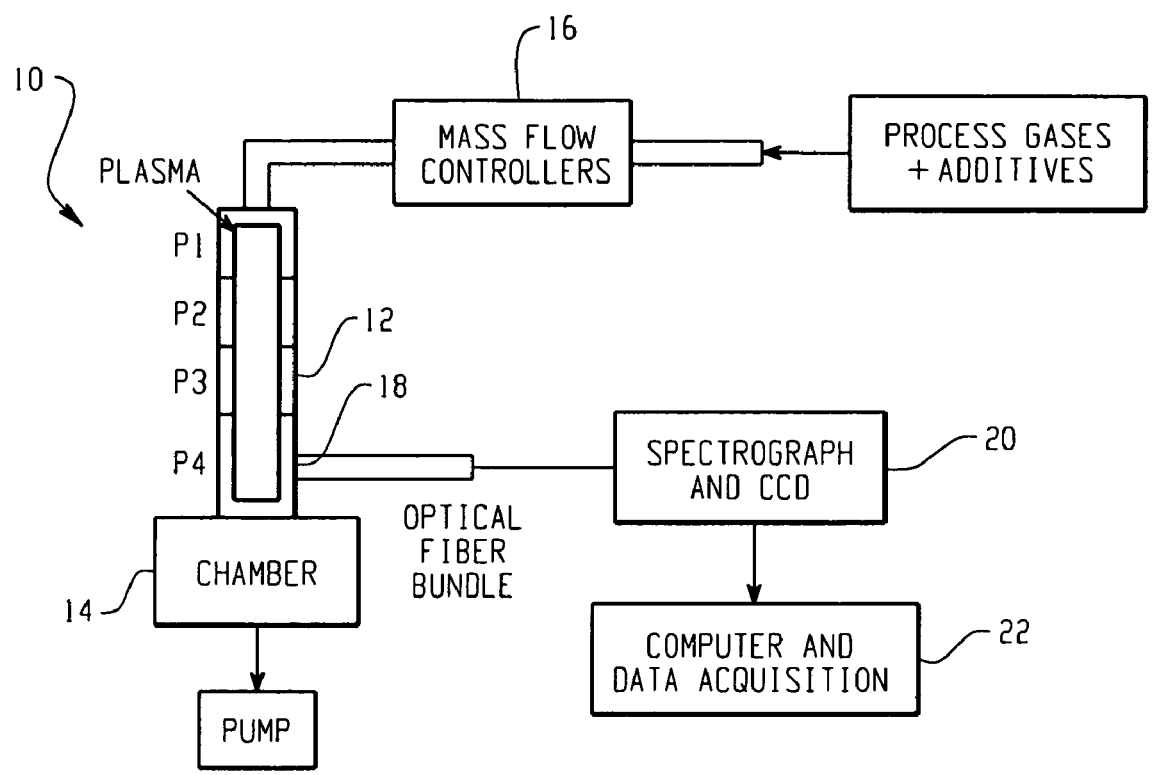
FIG. 7 schematically illustrates a plasma ashing apparatus including an optical emission spectrometer suitable for monitoring the emission signals in accordance with the present disclosure.

FIG. 7 illustrates an exemplary plasma asher apparatus generally designated 10. The illustrated plasma ashing apparatus is a downstream plasma asher and generally includes a plasma generating portion 12 fluidly coupled to a process chamber 14 at one end for processing a substrate with the plasma and a mass flow controller 16 at the other end for providing a mixture of gases for generating the plasma. The plasma generating portion also includes an optical port 18 to which an optical emission spectrometer is coupled in a conventional manner well known to those in the art. The spectrometer 20 itself can be a charge-coupled device for capturing the spectra in the manner described. A computer 22 then receives and processes the data. In a simpler form, the detection of two distinct wavelengths can also be accomplished by using two detectors and suitable optical filters.

The settings and optimization for particular plasma ashers will be well within the skill of those in the art in view of this disclosure. Plasma ashers generally are comprised of a plasma generating chamber and a plasma reaction chamber. For exemplary purposes only, in a 300 mm Fusion ES3 downstream plasma asher, the wafers are preferably heated in the reaction chamber to a temperature between room temperature and 450° C. More preferably, the wafers are heated to temperatures ranging from about 250° C. to about 350° C. The temperatures used during processing may be constant or alternatively, ramped or stepped during processing. Increasing the temperature is recognized by those skilled in the art as a method to increase the ashing rate.

The processing pressure within the reaction chamber is preferably about 1 torr or more. More preferably, the pressure is operated in a range from about 0.5 torr to about 4 torr. An excitable gas mixture is fed into the plasma-generating chamber via a gas inlet. The gas mixture is exposed to an energy source within the plasma-generating chamber, e.g., microwave energy, preferably between about 500 W and 5,000 W, to generate excited or energetic atoms from the gas mixture. The generated plasma is comprised of electrically neutral and charged particles formed from the gases used in the plasma gas mixture. The charged particles are selectively removed prior to plasma reaching the wafer. In one embodiment, the gas mixture for forming the plasma includes a hydrogen and helium gas mixture. In other embodiments, the gas mixture includes a mixture of hydrogen, helium, and fluorine gases. The gases employed to form the substantially oxygen and nitrogen-free plasma may include sufficient oxygen and/or nitrogen as a function of the purity of the gas, process chamber, or in the case of oxygen, deliberately added. The oxygen can be added as a pre-mixture with a noble gas. The total gas flow rate is preferably from about 500 to 12,000 standard cubic centimeters per minute (sccm) for the 300 mm downstream plasma asher. The photoresist, organic overlayers, and polymers/residues are selectively removed from the wafer by reaction with the excited or energetic atoms generated by the plasma. The reaction may be optically monitored for endpoint detection as is recognized by those in the art.

The foregoing descriptions of the preferred embodiments of the disclosure have been presented for purposes of illustration and description. It is not intended to be exhaustive or to limit the disclosure to the precise forms disclosed. Obvious modifications or variations are possible in light of the above teachings. The embodiments were chosen and described to provide the best illustration of the principles of the disclosure and its practical applications to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally and equitably entitled.

The invention claimed is:

1. A process for monitoring oxygen and/or nitrogen species in a substantially oxygen and nitrogen-free plasma ashing process of a substrate, the process comprising:
    forming reactive species by exposing a plasma gas composition to an energy source to form a plasma substantially free from nitrogen species and oxygen species;
    monitoring optical emission signals specifically associated with one or more major components of the plasma gas composition; and
    correlating perturbations in the monitored optical emission signals affected by the presence of oxygen and/or nitrogen species in the plasma gas composition to a specific amount of the oxygen and/or nitrogen species in the plasma.

2. The process according to claim 1, wherein the one or more major components of the plasma gas composition consists essentially of hydrogen-bearing gas and a noble gas.

3. The process according to claim 2, wherein the noble gas is helium.

4. The process according to claim 1, wherein correlating the perturbations in the emission signals comprises monitoring changes in a ratio of a hydrogen (H or $H_2$) emission signal to a helium emission signal affected by different amounts of the oxygen and/or nitrogen species in the plasma.

5. The process according to claim 1, wherein correlating the perturbations in the emission signals comprises monitoring changes in a ratio of a hydrogen radical (H) emission signal to a molecular hydrogen ($H_2$) emission signal or to a helium (He) emission signal affected by different amounts of the oxygen and/or nitrogen species in the plasma.

6. The process according to claim 1, wherein the substrate comprises a carbon containing insulating layer having a dielectric constant less than 3.0.

7. The process according to claim 1, wherein correlating the perturbations in the emission signals comprises monitoring changes in a broadband spectrum free of any major emission signal peaks as a function of oxygen and/or nitrogen in the plasma.

8. The process according to claim 1, further comprising maintaining the amount of the oxygen species during the substantially oxygen and nitrogen free plasma ashing process at about 5 parts per million to about 15 parts per million and the arrogant of the nitrogen species at less than about 1 part per million, except when a source for the oxygen species is shut off.

9. A process for monitoring oxygen and/or nitrogen species in a substantially oxygen and nitrogen-free plasma ashing process of a substrate, the process comprising:
    monitoring a first ratio of optical emission signals specifically associated with major components of the plasma gas composition in the presence of a fixed amount of oxygen and a second ratio in the absence of the fixed amount of oxygen; and
    calculating a third ratio based on the first to second ratios during the substantially oxygen and nitrogen-free plasma ashing process and correlating an amount of oxygen and nitrogen species in the plasma from a model curve using the third ratio.

10. The process of claim 9, wherein the major components of the plasma gas composition are helium and hydrogen.

11. The process according to claim 9, wherein the ratio of major components in the plasma is H/He.

12. The process according to claim 9, wherein the ratio of major components in the plasma is $H_2$/He.

13. The process according to claim 9, wherein the ratio of major components in the plasma is H/$H_2$.

14. The process according to claim 9, further comprising maintaining the amount of the oxygen species during the substantially oxygen and nitrogen free plasma ashing process at about 5 parts per million to about 15 parts per million and the amount of the nitrogen species at less than about 1 part per million, except when a source for the oxygen species shut off.

15. A process for monitoring nitrogen and/or oxygen species at levels less than 100 ppm in substantially oxygen and/or nitrogen free plasmas, the process comprising:
    measuring spectral perturbations produced by the oxygen and/or nitrogen species present at levels less than 100 ppm in the substantially oxygen and/or nitrogen free plasma on other species that define major components of the plasma; and
    correlating the spectral perturbation affected by the presence of the oxygen and/or nitrogen species in the plasma gas composition to a specific amount of oxygen and nitrogen in the plasma.

16. The process of claim 15, wherein the substantially oxygen and/or nitrogen free plasma is formed from a gas mixture comprising hydrogen and helium.

17. The process of claim 15, further comprising maintaining the amount of the oxygen during the substantially oxygen and nitrogen free plasma ashing process at about 5 parts per million to about 15 parts per million and the amount of the nitrogen at less than about 1 part per million, except when a source for the oxygen species is shut off.

18. A process for detecting contamination levels of nitrogen and oxygen in a gas mixture comprising helium and hydrogen, the process comprising:
    generating a plasma with the gas mixture;
    monitoring optical emission signals specifically associated with hydrogen and helium species in the plasma; and
    correlating perturbations in the monitored optical emission signals affected by the presence of oxygen and/or nitrogen species in the plasma gas composition to a specific amount of the oxygen and/or nitrogen species in the plasma.

19. The process of claim 18, wherein correlating the perturbations in the optical emission signals comprises monitoring changes in a ratio of the hydrogen (H or $H_2$) emission signal to the helium emission signal affected by different amounts of the oxygen and/or nitrogen species in the plasma.

* * * * *